(12) United States Patent
Stokes et al.

(10) Patent No.: US 8,133,217 B2
(45) Date of Patent: Mar. 13, 2012

(54) METHOD AND APPARATUS FOR MARKING A LUMENAL WALL

(75) Inventors: Michael J. Stokes, Cincinnati, OH (US); Thomas E. Albrecht, Cincinnati, OH (US); James R. Giordano, Milford, OH (US); Matthew D. Holcomb, Lebanon, OH (US); Mark S. Ortiz, Milford, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 986 days.

(21) Appl. No.: 12/113,779

(22) Filed: May 1, 2008

(65) Prior Publication Data

US 2009/0275937 A1  Nov. 5, 2009

(51) Int. Cl.
*A61B 18/18* (2006.01)
(52) U.S. Cl. ............... 606/33; 606/41; 606/32
(58) Field of Classification Search ............ 606/32–45, 606/151
See application file for complete search history.

(56) References Cited

U.S. PATENT DOCUMENTS

| | | | |
|---|---|---|---|
| 4,781,185 A * | 11/1988 | Kauphusman et al. | 606/2 |
| 5,797,878 A * | 8/1998 | Bleam | 604/196 |
| 6,440,128 B1 | 8/2002 | Edwards et al. | |
| 6,558,400 B2 | 5/2003 | Deem et al. | |
| 2002/0183768 A1 * | 12/2002 | Deem et al. | 606/151 |
| 2003/0153905 A1 * | 8/2003 | Edwards et al. | 606/41 |
| 2005/0096673 A1 | 5/2005 | Stack et al. | |
| 2005/0177176 A1 | 8/2005 | Gerbi et al. | |
| 2007/0118106 A1 | 5/2007 | Utley et al. | |

FOREIGN PATENT DOCUMENTS

EP   1938758   7/2008

* cited by examiner

*Primary Examiner* — Linda Dvorak
*Assistant Examiner* — Amanda Scott
(74) *Attorney, Agent, or Firm* — Welsh Flaxman & Gitler LLC

(57) ABSTRACT

A marking apparatus includes a selectively inflatable balloon. The balloon includes an external lumen adapted for connection to a vacuum source. The external lumen includes ports for creating a vacuum at the ports sufficient to draw walls of the gastric cavity into contact with the external lumen. The balloon is further provided with RF energy delivery devices. In accordance with an alternate embodiment, a marking apparatus includes an elongated, hollow body, the hollow body including a proximal end and a distal end. The hollow body includes at least one suction trough in which a plurality of holes is disposed to draw suction on tissue. The at least one suction trough extends along a substantial portion of the hollow body as it extends from its distal end to its proximal end.

4 Claims, 5 Drawing Sheets

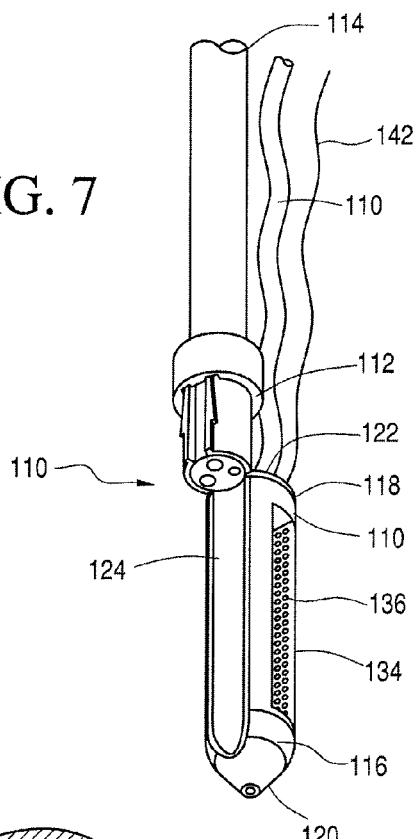
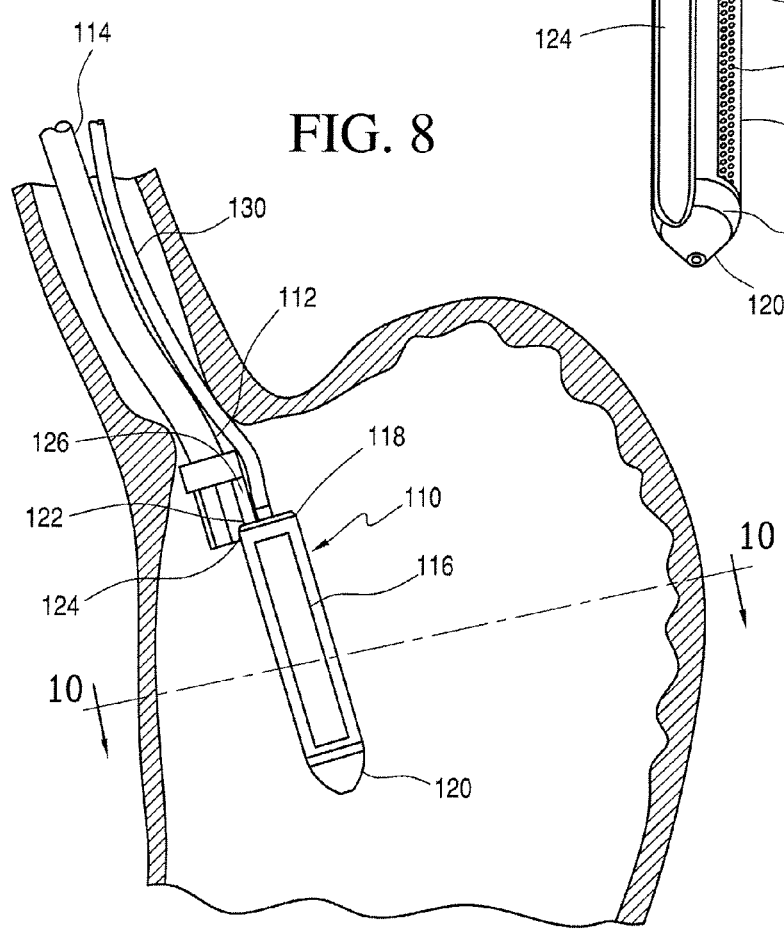
FIG. 7
FIG. 8

METHOD AND APPARATUS FOR MARKING A LUMENAL WALL

BACKGROUND OF THE INVENTION

1. Field of the Invention

The invention relates to a method and apparatus for gastric surgery. More particularly, the invention relates to a method and apparatus for marking the gastric cavity in the creation of a pouch during gastric reduction surgery.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated that the costs relating to obesity are in excess of 100 billion dollars in the United States alone. Studies have shown that conservative treatment with diet and exercise alone may be ineffective for reducing excess body weight in many patients.

Bariatrics is the branch of medicine that deals with the control and treatment of obesity. A variety of surgical procedures have been developed within the bariatrics field to treat obesity. The most common currently performed procedure is the Rouxen-Y gastric bypass (RYGB). This procedure is highly complex and is commonly utilized to treat people exhibiting morbid obesity. In an RYGB procedure a small gastric cavity pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the gastric cavity to form an hourglass shape. This procedure restricts the amount of food that passes from one section of the gastric cavity to the next, thereby inducing a feeling of satiety. A band is placed around the gastric cavity near the junction of the gastric cavity and esophagus. The small upper gastric cavity pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

With the foregoing in mind, it is desirable to have a surgical weight loss procedure that is inexpensive, with few potential complications, and that provides patients with a weight loss benefit while buying time for the lifestyle changes necessary to maintain the weight loss. Further, it is desirable that the procedure be minimally invasive to the patient, allowing for a quick recovery and less scarring. For example, when creating a restrictive pouch in the gastric cavity for bariatric procedures, it is desirable to create the pouch in a predictable and repeatable manner. This is difficult when using individually delivered endolumenal fasteners due to the nature of the endolumenal procedure and the unpredictable nature of the gastric cavity. The present invention provides a method and apparatus for improving upon such procedures.

SUMMARY OF THE INVENTION

It is, therefore, an object of the present invention to provide a marking apparatus. The marking apparatus includes a selectively inflatable balloon. The balloon includes an external lumen adapted for connection to a vacuum source. The external lumen includes ports for creating a vacuum at the ports sufficient to draw walls of the gastric cavity into contact with the external lumen. The balloon is further provided with RF energy delivery devices.

It is also an object of the present invention to provide a marking apparatus wherein the balloon is secured at the distal end of a hollow tube.

It is another object of the present invention to provide a marking apparatus wherein a seal is provided within the hollow tube.

It is a further object of the present invention to provide a marking apparatus wherein the balloon is transparent.

It is also an object of the present invention to provide a marking apparatus wherein the balloon includes an anterior wall and a posterior wall. The anterior wall and the posterior wall are connected by a flat edge member that runs about the circumference of the balloon.

It is another object of the present invention to provide a marking apparatus wherein the RF energy delivery devices are positioned adjacent the ports and spaced along the edge member.

It is a further object of the present invention to provide a marking apparatus wherein the edge member is shaped and dimensioned to engage anterior and posterior walls of the gastric cavity at locations where the desired gastric pouch should be formed.

It is also an object of the present invention to provide a marking apparatus wherein the external lumen is formed along the anterior and posterior walls adjacent the edge member.

It is another object of the present invention to provide a marking apparatus wherein the ports in the external lumen are provided on anterior and posterior facing sides of the external lumen for creating a vacuum at the ports along the anterior and posterior walls of the balloon sufficient to draw the anterior and posterior walls of the gastric cavity into contact with the external lumen.

It is a further object of the present invention to provide a marking apparatus including an elongated, hollow body, the hollow body including a proximal end and a distal end. The hollow body includes at least one suction trough in which a plurality of holes are disposed to draw suction on tissue. The at least one suction trough extends along a substantial portion of the hollow body as it extends from its distal end to its proximal end.

It is also an object of the present invention to provide a marking apparatus wherein the proximal end of the hollow body is secured to the distal end of the gastroscope.

It is another object of the present invention to provide a marking apparatus wherein a suction tube is also connected to the proximal end of the elongated, hollow body. The suction tube extends from the hollow body to a proximal vacuum source creating a vacuum within the hollow body.

It is a further object of the present invention to provide a marking apparatus wherein the hollow body includes a first suction trough and a second suction trough, and the first suction trough and the second suction trough are disposed on opposite sides of the hollow body.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 7 is a perspective view of a marking apparatus in accordance with an alternate embodiment of the present invention.

FIGS. 8, 9 and 10 show the steps associated with marking the gastric cavity in accordance with the alternate embodiment of present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the various figures, the present invention provides methods and apparatuses for creating markings in the anterior and posterior portions of the gastric cavity for subsequent guidance during the fastening procedure. The present invention provides a mechanism for placing these markings along the anterior and posterior portions of the gastric cavity in a predictable and repeatable manner ensuring the final size and shape of the resulting restrictive pouch is proper and is shaped as desired by the medical practitioner. Once the markings are applied in accordance with the present invention, fasteners, such as T-tag fasteners are applied at the marked locations to securely hold the anterior and posterior walls in apposition. The markings may be used during a reduction procedure such as disclosed in co-pending application Ser. No. 11/779,322 which is incorporated herein by reference.

Figure 1:
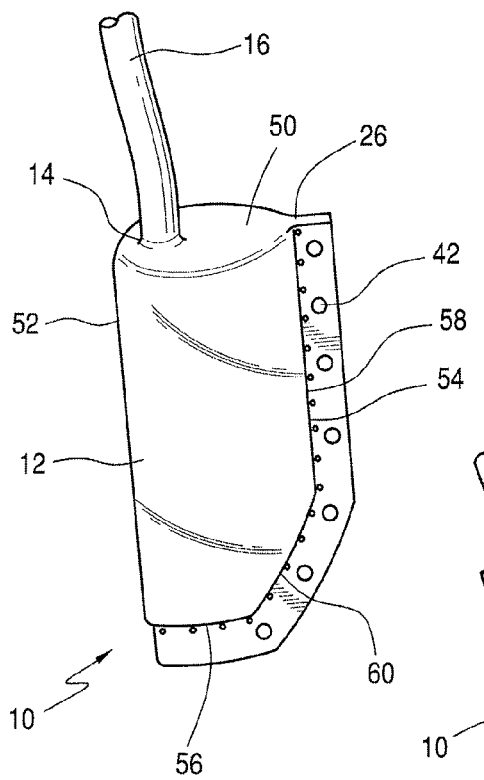
FIG. 1 is a perspective view of a marking apparatus in accordance with the present invention.
Figure 2:
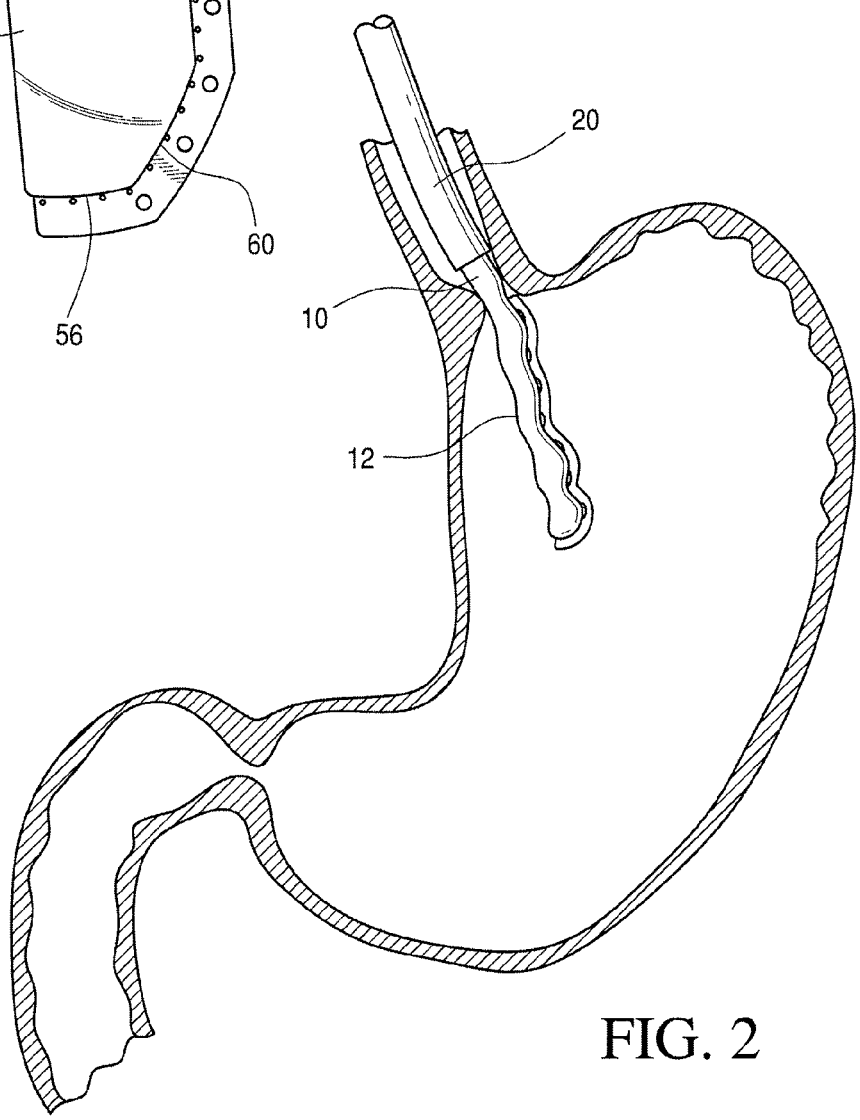
FIGS. 2, 3, 4, 5 and 6 show the steps associated with marking the gastric cavity in accordance with the present invention.
Figure 3:
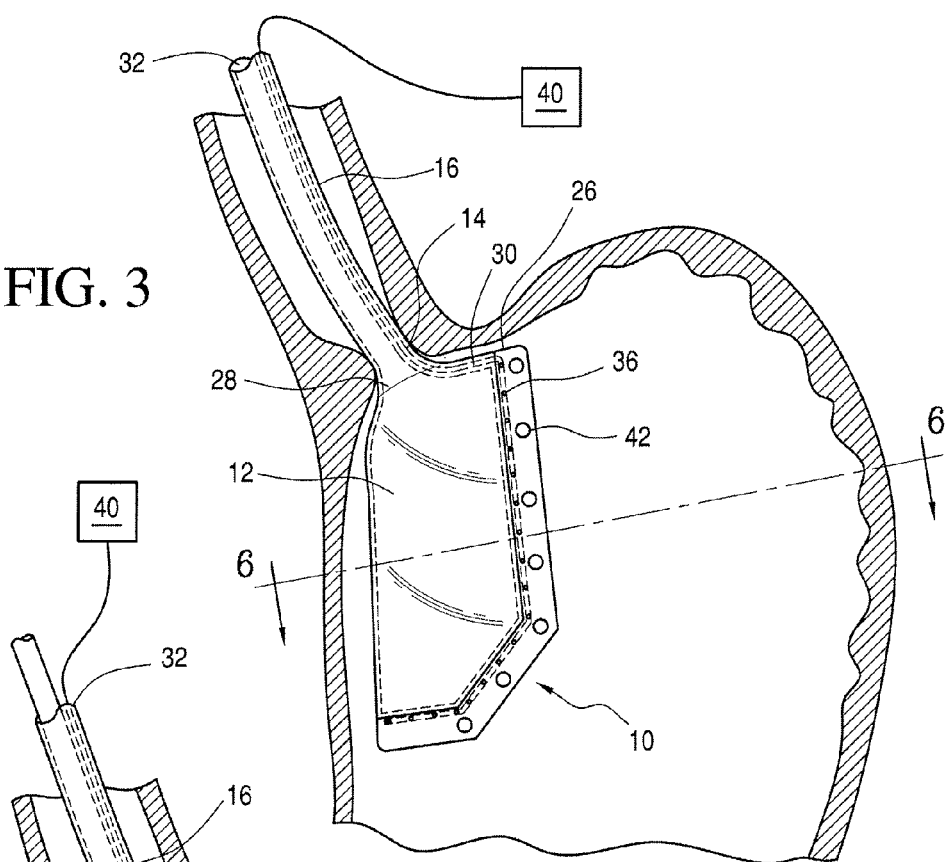
Figure 4:
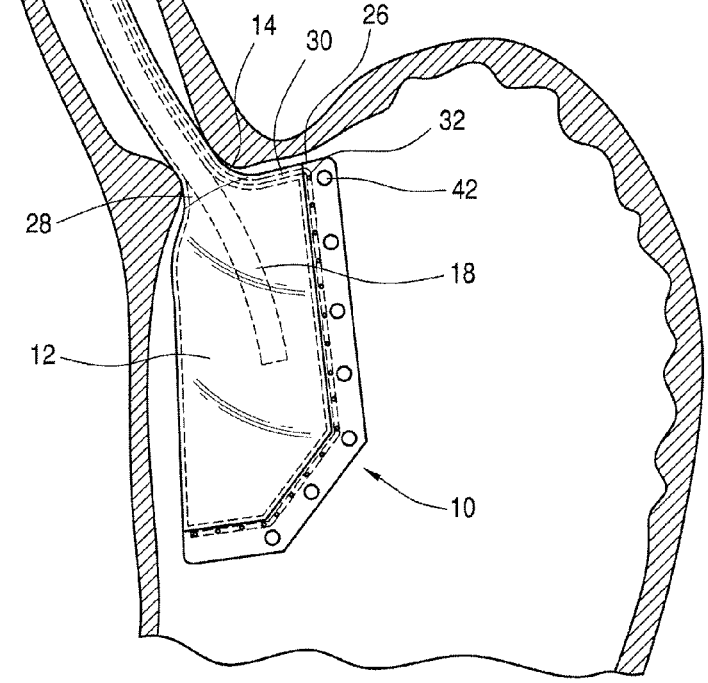

In accordance with a preferred embodiment, and with reference to FIGS. 1 to 6, a marking apparatus 10 composed of a selectively inflatable balloon 12 at the distal end 14 of a hollow tube 16 is disclosed. The marking apparatus 10 is shaped and dimensioned for insertion of the balloon 12 into the gastric cavity. The collapsed balloon 12 is inserted transorally through an endoscope or overtube 20, as best shown in FIG. 2. The hollow tube 16 and balloon 12 are shaped and dimensioned for accepting a typical gastroscope 18 to permit visualization during the intubation process; that is, and as will be discussed below in greater detail, the hollow tube 16 is shaped and dimensioned to permit the passage of the gastroscope 18 therethrough for viewing from within the balloon 12 at the distal end 14 of the hollow tube 16.

The balloon 12 is transparent and inflated in the gastric cavity using a pressure source (not shown) coupled to hollow tube 16. As will be appreciated based upon the following disclosure, the balloon 12 is shaped to substantially resemble the desired pouch a medical practitioner wishes to form within the gastric cavity. As such, the balloon 12 includes an anterior wall 22 and a posterior wall 24. The anterior wall 22 and the posterior wall 24 are connected by an edge member 26 that runs about a portion of the circumference of the balloon 12 (that is, the circumference of the balloon 12 when viewed normal to either the anterior wall 22 or the posterior wall 24 of the balloon 12). In accordance with a preferred embodiment of the present invention, the shape of the balloon 12 is configured to resemble the gastric pouch after a gastric bypass, more particularly, a gastric pouch following the lesser curve of the stomach. Alternatively, it is contemplated the balloon 12 may be shaped to configure the stomach to resemble a vertical gastroplasty or sleeve gastrectomy.

With this in mind, the balloon 12, when viewed normal to a plane in which its widest dimensions when inflated lies, defines a parallelogram including a top edge 50 from which the hollow tube 16 extends for connecting the balloon 12 to a power source and vacuum source as discussed below in greater detail. Extending downwardly from the top edge 50 are a first lateral side edge 52 (which is shaped and dimensioned for positioning along the lesser curve of the stomach with the anterior wall 22 and the posterior wall 24 of the balloon 12 respectively applying pressure to the anterior gastric cavity wall and the posterior gastric cavity wall when the balloon 12 is inflated) and a second opposite lateral side edge 54; when looking at the anterior wall 22 of the balloon 12 as shown in FIG. 1, the first lateral side edge 52 lies on the left side of the balloon 12 and the second lateral side edge 54 lies on the right side of the balloon 12. The first lateral side edge 52 extends at approximately a right angle from the top edge 50, and extends from the top edge 50 to the bottom edge 56 along a substantially straight line. The second lateral side edge 54 also extends from the top edge 50 to the bottom edge 56, however, the second lateral side edge 54 includes an upper section 58 and a lower section 60. The upper section 58 extends from the top edge 50 at approximately a right angle, while the lower section 60 of the second lateral side edge 54 is oriented at an oblique angle (approximately 160 degrees) relative to the upper section 58 of the second lateral side edge 54 such that it extends from the upper section 58 of the second lateral side edge 54 to the bottom edge 56. It is further contemplated that the second lateral side edge 54 could be curved along its length.

With the foregoing description of the balloon 12 in mind, and considering the use of the balloon 12 as discussed below in greater detail, the edge member 26 is formed along the second lateral side edge 54 and continues along the bottom edge 56 of the balloon 12.

A seal 28 is provided within the hollow tube 16. The seal 28 is constructed to prevent air from escaping from the balloon 12 and allows for controlled inflation of the balloon 12. In accordance with a preferred embodiment of the present invention, the seal may be a duck bill seal, o-ring, lip seal, or other standard type of seal known to those skilled in the art. With the balloon 12 inflated within the gastric cavity, the gastroscope 18 is inserted through the hollow tube 16 and into the cavity defined by the balloon 12. Once again, the seal 28 within the hollow tube 16 allows for insertion of the gastroscope 18 through the hollow tube 16 and into the balloon 12 without releasing the pressure used to inflate the balloon 12.

With the gastroscope 18 within the balloon 12, the medical practitioner may view the gastric cavity wall through the clear balloon 12, and the balloon 12 is positioned against the lesser curve just distal to the esophagogastric junction. That is, the balloon 12 is positioned at the location wherein the medical practitioner will be forming the gastric cavity pouch used in the gastric reduction procedure.

The balloon 12 is further provided with an external lumen 30 formed along the anterior and posterior walls 22, 24 adjacent the edge member 26. As such, the external lumen 30 runs from the proximal end 32 of the hollow tube 16 where it is connected to a vacuum source 40 down through the length of the edge member 26. The external lumen 30 is provided with anterior and posterior facing ports 36, 38 extending thereal-ong, and the external lumen 30 is coupled to a vacuum source 40 at the proximal end 32 of the hollow tube 16 for creating a vacuum at the anterior and posterior facing ports 36, 38 sufficient to draw the anterior and posterior walls of the gastric cavity into contact with the external lumen 30 and the edge member 26.

The edge member 26 is relatively flat such that both the anterior and posterior walls of the gastric cavity will come into contact therewith when a vacuum is applied thereto in accordance with the present invention. In fact, the edge member 26 is shaped and dimensioned to engage the anterior and posterior walls of the gastric cavity at locations where the desired gastric pouch should be formed. The external lumen 30 is positioned opposite the lesser curve, with the anterior and posterior portions of the gastric cavity on opposite sides thereof.

Once the balloon 12 is properly positioned and the position is verified using a gastroscope 18, a vacuum is drawn through the anterior and posterior facing ports 36, 38 of the external lumen 30 drawing the anterior and posterior walls of the gastric cavity together near the lesser curve opposing the anterior and posterior portions of the gastric cavity. Final and proper positioning of the balloon 12 is once again verified through the utilization of the gastroscope 18.

Figure 5:
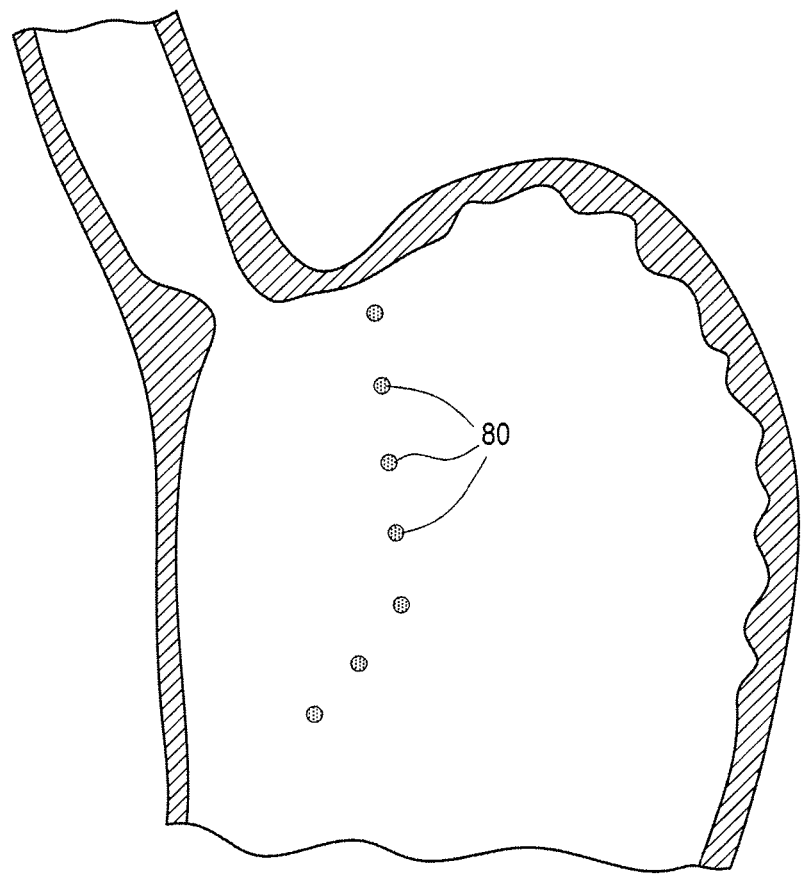
Figure 6:
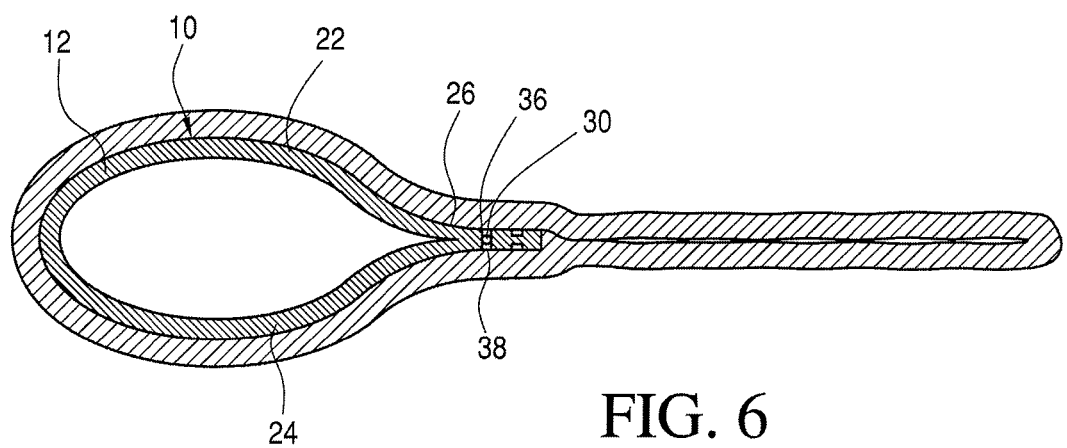
Figure 9:
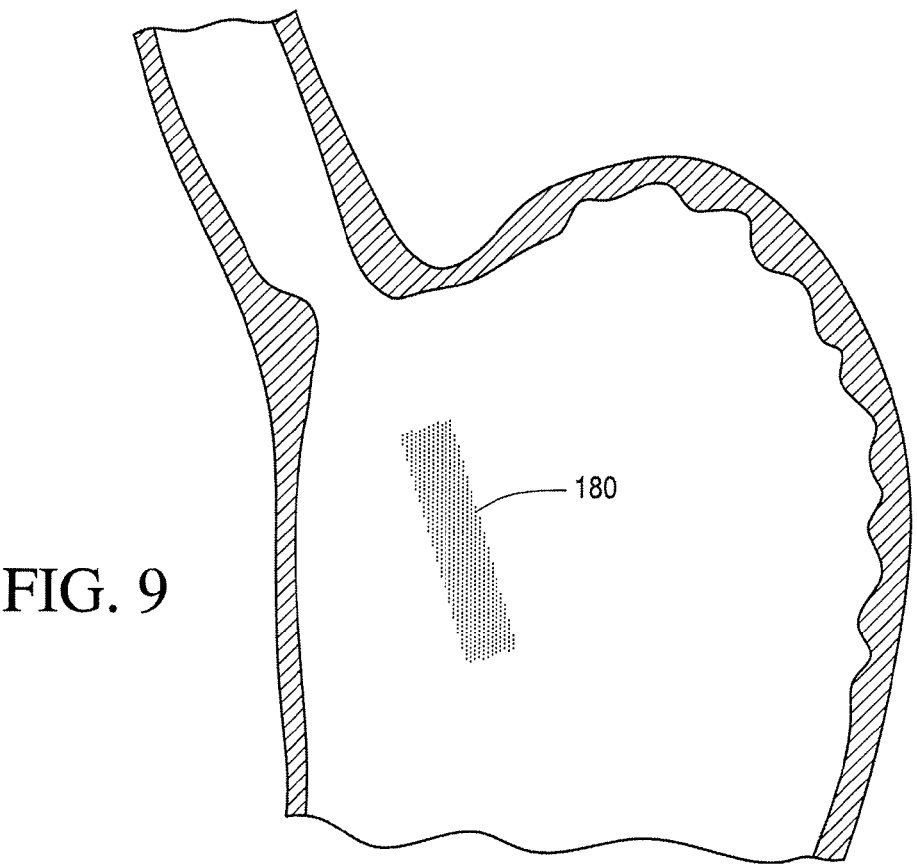
Figure 10:
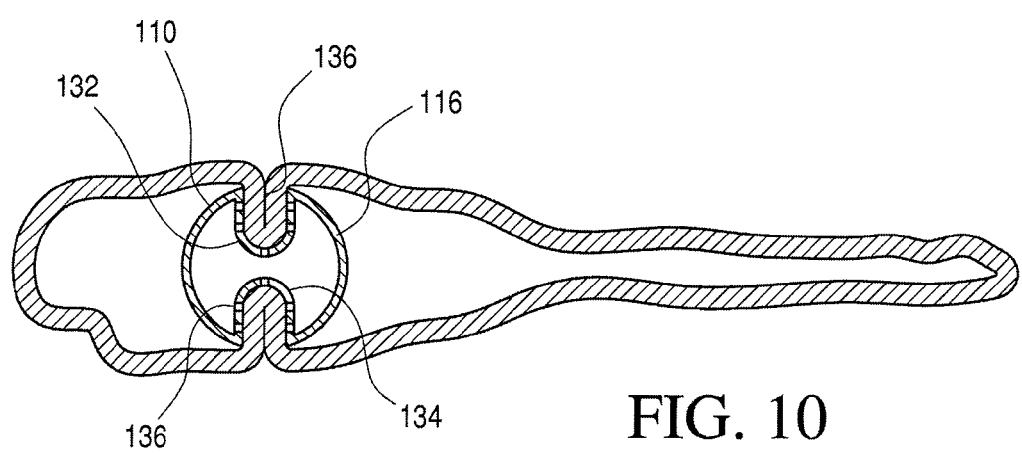

The balloon 12 is further provided with RF energy delivery devices 42 along the edge member 26 at positions adjacent the anterior and posterior facing ports 36, 38. That is, anterior and posterior facing RF energy delivery devices 42 are positioned, spaced along the external surface of the edge member 26. As such, when the RF energy delivery devices 42 are activated, RF energy is delivered to the anterior and posterior portions of the gastric cavity near the anterior and posterior facing ports 36, 38 at discrete locations to create burn marks 80, as seen in FIG. 5, by the heating and burning of the affected tissue. The burn marks 80 are left in the mucosal layer where subsequent fastening is desired. The burn marks provide an identification of the desired location for subsequent procedures. Once the marks are created, the balloon 12 may be deflated and removed.

In accordance with an alternate embodiment, and with reference to FIGS. 7 to 10, tissue marking is achieved utilizing a marking apparatus 110 secured adjacent to the distal end 112 of a conventional gastroscope 114. As discussed above, tissue marking is important for endoscopic procedures in order to guide instruments to desired targets. It is contemplated such marking apparatuses can benefit endoscopic suturing devices during gastric restriction procedures or other targeted procedures.

In accordance with this preferred embodiment, and with reference to FIGS. 7 to 10, the present marking apparatus 110 is comprised of an elongated, hollow body 116. The hollow body 116 includes a proximal end 118 and a distal end 120. The proximal end 118 is secured to the distal end 112 of the gastroscope 114 using a simple collar clamp 122 which is held fast to the gastroscope 114 by the sliding of a wedge 124 over a dovetail 126 formed in the gastroscope 114 which forces the clamp 122 to contract onto the gastroscope 114. Other coupling structures such as those disclosed in commonly owned U.S. patent application Ser. No. 11/394,163, entitled "SURGICAL SUTURING APPARATUS WITH COLLAPSIBLE VACUUM CHAMBER", filed Mar. 31, 2006, which is incorporated herein by reference, may be employed without departing from the spirit of the present invention. A suction tube 130 is also connected to the proximal end 118 of the elongated, hollow body 116 of the present marking apparatus 110. The suction tube 130 extends from the hollow body 116 to a proximal vacuum source 128 for creating a vacuum within the hollow body 116 for use of the present marking apparatus 110 in a manner to be discussed below in greater detail. It is contemplated the suction tube 130 may be inserted through a working channel of the gastroscope 114 or it may travel alongside the gastroscope 114 (see FIGS. 7 and 8).

The hollow body 116 of the marking apparatus 110 is provided with at least one suction trough 132, 134 in which a plurality of holes 136 are disposed to draw suction on the tissue where suturing is to take place. The at least one suction trough 132, 134 extends along a substantial portion of the hollow body 116 as it extends from its distal end 120 to its proximal end 118. In accordance with a preferred embodiment specifically adapted for gastric restriction procedures, a first suction trough 132 and a second suction trough 134 are disposed on opposite sides of the hollow body 116. By orienting the first and second suction troughs 132, 134 on opposite sides of the hollow body 116 the present marking apparatus 110 is capable of acquiring both the posterior and anterior walls of the gastric cavity.

It is contemplated insertion of the present marking apparatus 110 may be aided by constructing the hollow body 116 thereof from a flexible material. Control of the orientation of the present marking apparatus 110 is affected by attaching the marking apparatus 110 to the distal end 112 of the gastroscope 114 as discussed above.

In practice, suction is applied to the hollow body 116 drawing tissue into contact with the first and second suction troughs 132, 134. If suction is drawn for a period of time, typically 30 seconds to 1 minute, a suction mark 180 is produced on the tissue to aid in guiding future devices, see FIG. 9. It is further contemplated marking may be enhanced by the provision of an RF energy source 142 within the suction troughs 132, 134.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and/or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A marking apparatus, comprising:
a selectively inflatable balloon including an anterior wall and a posterior wall, the anterior wall and posterior wall are connected by an edge member that runs about a portion of the circumference of the balloon;
a hollow tube extends from the balloon for connecting the balloon to a power source and vacuum source;
an external lumen is formed along the anterior wall and posterior wall adjacent the edge member, the external lumen running from a proximal end of the hollow tube down through the length of the edge member, the external lumen being provided with anterior and posterior facing ports extending therealong, wherein the external lumen is coupled to a vacuum source at the proximal end of the hollow tube for creating a vacuum at the anterior and posterior facing ports sufficient to draw anterior and posterior walls of the gastric cavity into contact with the external lumen and the edge member; and
RF energy delivery devices are positioned along the edge member adjacent the anterior and posterior facing ports, the RF energy delivery devices create burn marks by the heating and burning affected tissue.

2. The marking apparatus according to claim 1, further including a gastroscope shaped and dimensioned to pass through the hollow tube and into the balloon.

3. The marking apparatus according to claim 2, wherein a seal is provided within the hollow tube, the seal being constructed to prevent air from escaping from the balloon and allow for controlled inflation of the balloon such that the gastroscope may pass through the hollow tube and into the balloon without releasing the pressure used to inflate the balloon.

4. The marking apparatus according to claim 1, wherein the balloon is transparent.

\* \* \* \* \*